(12) United States Patent
Sarig-Bahat

(10) Patent No.: US 8,679,037 B2
(45) Date of Patent: Mar. 25, 2014

(54) MOTION ASSESSMENT SYSTEM AND METHOD

(76) Inventor: Hilla Sarig-Bahat, Kerem MaHaral (IL)

( * ) Notice: Subject to any disclaimer, the term of this patent is extended or adjusted under 35 U.S.C. 154(b) by 0 days.

(21) Appl. No.: 13/131,871

(22) PCT Filed: Dec. 2, 2009

(86) PCT No.: PCT/IL2009/001135
§ 371 (c)(1),
(2), (4) Date: May 30, 2011

(87) PCT Pub. No.: WO2010/064237
PCT Pub. Date: Jun. 10, 2010

(65) Prior Publication Data
US 2011/0230792 A1    Sep. 22, 2011

Related U.S. Application Data

(60) Provisional application No. 61/119,397, filed on Dec. 3, 2008, provisional application No. 61/184,854, filed on Jun. 8, 2009.

(51) Int. Cl.
*A61B 5/103* (2006.01)
*A61B 5/11* (2006.01)

(52) U.S. Cl.
USPC ............ 600/595; 600/587; 600/591; 128/898

(58) Field of Classification Search
USPC ........................... 600/587, 591, 595; 128/898
See application file for complete search history.

(56) References Cited

U.S. PATENT DOCUMENTS

| | | | | |
|---|---|---|---|---|
| 3,068,859 A | * | 12/1962 | Treutelaar | 602/32 |
| 4,665,928 A | * | 5/1987 | Linial et al. | 600/595 |
| 4,912,638 A | * | 3/1990 | Pratt, Jr. | 600/595 |
| 5,099,859 A | * | 3/1992 | Bell | 600/594 |
| 5,203,346 A | * | 4/1993 | Fuhr et al. | 600/594 |
| 5,498,218 A | * | 3/1996 | Proctor et al. | 482/10 |
| 5,544,649 A | * | 8/1996 | David et al. | 600/301 |
| 5,577,982 A | * | 11/1996 | Wells et al. | 482/10 |
| 5,758,658 A | * | 6/1998 | Petragallo | 600/595 |
| 5,891,060 A | * | 4/1999 | McGregor et al. | 600/595 |
| 5,954,674 A | * | 9/1999 | Fuhr | 600/594 |
| 5,961,474 A | * | 10/1999 | Reis | 600/595 |
| 5,991,701 A | * | 11/1999 | Triano | 702/150 |
| 5,997,440 A | * | 12/1999 | Hanoun | 482/10 |
| 6,007,459 A | * | 12/1999 | Burgess | 482/4 |
| 6,267,733 B1 | * | 7/2001 | Peterson et al. | 600/587 |
| 6,409,685 B1 | * | 6/2002 | Merzenich et al. | 600/587 |
| 6,774,885 B1 | * | 8/2004 | Even-Zohar | 345/156 |
| 6,984,208 B2 | * | 1/2006 | Zheng | 600/438 |
| 7,074,198 B2 | * | 7/2006 | Krullaards | 600/587 |
| 7,292,151 B2 | * | 11/2007 | Ferguson et al. | 340/573.1 |
| 7,556,607 B2 | * | 7/2009 | Coates et al. | 602/18 |
| 7,591,760 B2 | * | 9/2009 | Gordon et al. | 482/8 |
| 7,862,477 B2 | * | 1/2011 | Cunningham et al. | 482/8 |

(Continued)

*Primary Examiner* — Sean Dougherty
(74) *Attorney, Agent, or Firm* — Roach Brown McCarthy & Gruber, P.C; Kevin D. McCarthy

(57) ABSTRACT

A system and method of motion assessment for use in medical analysis and treatment of motion impairments. The system is configured to stimulate, monitor and analyze voluntary movements of a subject. A surround-display is used to stimulate movement of the subject, a motion tracker monitors the movements of the subject, and a processor receives data from the motion tracker and may be configured to control the surround-display.

10 Claims, 14 Drawing Sheets

(56) References Cited

U.S. PATENT DOCUMENTS

| | | | |
|---|---|---|---|
| 8,007,450 B2 * | 8/2011 | Williams | 600/595 |
| 8,113,991 B2 * | 2/2012 | Kutliroff | 482/8 |
| 8,469,865 B2 * | 6/2013 | Verheem | 482/110 |
| 8,529,480 B2 * | 9/2013 | Dicerbo et al. | 601/25 |
| 2003/0135129 A1 * | 7/2003 | Cusimano et al. | 600/546 |
| 2003/0149379 A1 * | 8/2003 | Krullaards | 600/587 |
| 2006/0247557 A1 * | 11/2006 | Coates et al. | 600/595 |
| 2007/0270727 A1 * | 11/2007 | Khorassani Zadeh | 601/120 |
| 2008/0009772 A1 * | 1/2008 | Tyler et al. | 600/595 |
| 2008/0027758 A1 * | 1/2008 | Cunningham et al. | 705/2 |
| 2008/0220874 A1 * | 9/2008 | Tatsumi et al. | 463/42 |
| 2008/0222318 A1 * | 9/2008 | Yoshioka | 710/31 |
| 2008/0226179 A1 * | 9/2008 | Dohta | 382/232 |
| 2009/0005709 A1 * | 1/2009 | Gagne | 600/594 |
| 2009/0306548 A1 * | 12/2009 | Bhugra et al. | 600/587 |
| 2011/0201904 A1 * | 8/2011 | Cusimano Reaston et al. | 600/301 |
| 2011/0230792 A1 * | 9/2011 | Sarig-Bahat | 600/595 |
| 2011/0295378 A1 * | 12/2011 | Bojarski et al. | 623/20.35 |

* cited by examiner

Figure 6

| CHARACTERISTIC | PATIENT GROUP (N=25) | CONTROL GROUP (N=42) |
|---|---|---|
| AGE IN YEARS (MEAN (SD), RANGE) | 39.0 (12.7), 22 - 65 | 35.3 (12.4), 23 - 64 |
| NO. OF FEMALES / MALES | 16 / 9 | 31 / 11 |
| DURATION IN MONTHS (MEAN, SD, RANGE) | 43.40 (53), 1.5 - 240 | NOT APPLICABLE |
| NO. OF CASES WITH RIGHT / LEFT / BILATERAL SYMPTOMS | 12 / 6 / 7 | NOT APPLICABLE |
| NO. OF CASES WITH / WITHOUT WHIPLASH INJURY | 7 / 18 | NOT APPLICABLE |
| NECK DISABILITY INDEX (MEAN (SD), RANGE) | 11.60 (4.88), 3 - 23 | NOT APPLICABLE |
| TAMPA SCALE OF KINESIOPHOBIA (MEAN (SD), RANGE) | 35.74 (5.71), 25 - 53 | NOT APPLICABLE |
| VISUAL ANALOGUE SCALE (MEAN (SD), RANGE) | 3.30 (2.05), 0 - 9 | NOT APPLICABLE |

Figure 9

| MOTION / STAGE | CONTROL GROUP (N=42) | | | PATIENT GROUP (N=25) | | |
|---|---|---|---|---|---|---|
| | CONV1 | VR | CONV2 | CONV1 | VR | CONV2 |
| FLEXION | 58.4 ± 11.5 | 56.0 ± 11.8 | 63.7 ± 11.2 | 46.1 ± 16.4 | 67.6 ± 11.8 | 58.2 ± 14.5 |
| EXTENSION | 44.3 ± 10.9 | 70.8 ± 13.1 | 47.2 ± 12.4 | 43.1 ± 15.0 | 67.0 ± 11.5 | 45.0 ± 14.7 |
| FLEXION+EXTENSION | 102.7 ± 15.7 | 126.8 ± 16.1 | 110.9 ± 14.1 | 89.2 ± 25.2 | 111.4 ± 22.8 | 103.1 ± 24.0 |
| RIGHT ROTATION | 66.3 ± 7.5 | 75.7 ± 6.5 | 68.9 ± 7.8 | 57.5 ± 12.5 | 50.0 ± 10.5 | 60.3 ± 11.2 |
| LEFT ROTATION | 66.7 ± 6.6 | 78.3 ± 6.9 | 69.1 ± 7.5 | 59.2 ± 11.0 | 61.4 ± 15.3 | 62.8 ± 10.5 |
| RIGHT+LEFT ROTATION | 133.1 ± 12.3 | 154.0 ± 11.8 | 138.0 ± 11.5 | 116.7± 21.1 | 134.6 ± 22.0 | 123.1 ± 19.9 |

CONV1- FIRST CONVENTIONAL ASSESSMENT

VR - ASSESSMENT IN THE VIRTUAL ENVIRONMENT (USING THE SYSTEM)

CONV2- SECOND CONVENTIONAL ASSESSMENT

FIGURE 11

|  | F+E VR | RR+LR VR | RR+LR CONV. | F+E CONV. |
|---|---|---|---|---|
| MODEL SIG. | 0.002 | <0.0001 | 0.0002 | 0.009 |
| PREDICTOR SIG. | 0.006 | 0.001 | 0.001 | 0.015 |
| OPTIMAL PREDICTOR VALUE | 133.3 | 146.0 | 119.3 | 81.8 |
| UNIT ODDS RATIO | 0.96 | 0.92 | 0.94 | 0.97 |
| 95% ODDS RATIO (CI) | 0.93 - 0.99 | 0.88 - 0.97 | 0.90 - 0.98 | 0.94 - 0.99 |
| SENSITIVITY | 0.88 | 0.72 | 0.56 | 0.40 |
| SPECIFICITY | 0.43 | 0.79 | 0.88 | 0.88 |
| ACCURACY | 0.31 | 0.51 | 0.44 | 0.28 |

Figure 13

| DIRECTION | FLEXION | | EXTENSION | |
|---|---|---|---|---|
| GROUP | CONTROL | PATIENTS | CONTROL | PATIENTS |
| RESPONSE TIME (S) | 0.12 (0.07) | 0.13 (0.06) | 0.16 (0.08) | 0.14 (0.08) |
| MOVEMENT TIME (S) | 1.15 (0.35) | 1.44 (0.44) | 1.27 (0.37) | 1.59 (0.53) |
| PEAK VELOCITY (°/S) | 105.0 (43.0) | 69.8 (34.7) | 138.6 (52.7) | 81.4 (39.7) |
| MEAN VELOCITY (°/S) | 33.3 (12.6) | 24.4 (9.1) | 46.5 (16.3) | 29.1 (12.4) |
| NO. VELOCITY PEAKS | 5.0 (1.7) | 6.1 (2.6) | 4.8 (1.8) | 5.9 (2.1) |
| TTP % | 67.1 (8.1) | 67.5 (12.2) | 63.6 (11.9) | 60.5 (13.5) |

| DIRECTION | RIGHT ROTATION | | LEFT ROTATION | |
|---|---|---|---|---|
| GROUP | CONTROL | PATIENTS | CONTROL | PATIENTS |
| RESPONSE TIME (S) | 0.20 (0.09) | 0.17 (0.09) | 0.15 (0.07) | 0.14 (0.06) |
| MOVEMENT TIME (S) | 1.17 (0.30) | 1.47 (0.49) | 1.23 (0.33) | 1.73 (0.66) |
| PEAK VELOCITY (°/S) | 162.2 (56.6) | 100.2 (43.6) | 165.9 (51.9) | 108.5 (48.3) |
| MEAN VELOCITY (°/S) | 55.0 (15.9) | 39.8 (16.2) | 56.4 (13.6) | 36.9 (15.2) |
| NO. VELOCITY PEAKS | 3.6 (1.4) | 4.9 (2.8) | 4.2 (1.8) | 6.1 (3.3) |
| TTP % | 64.1 (12.5) | 62.2 (11.2) | 68.1 (10.1) | 62.3 (11.7) |

Figure 14

| DIRECTION | FLEXION | | EXTENSION | |
|---|---|---|---|---|
| | IMPAIRMENT PERCENTAGE | P VALUE | IMPAIRMENT PERCENTAGE | P VALUE |
| RESPONSE TIME (S) | NS | 0.181 | NS | 0.230 |
| MOVEMENT TIME (S) | 25 | 0.002 | 25 | 0.002 |
| PEAK VELOCITY (°/S) | -34 | <0.0001 | -41 | <0.0001 |
| MEAN VELOCITY (°/S) | -27 | 0.001 | -38 | <0.0001 |
| NO. VELOCITY PEAKS | 22 | 0.018 | 24 | 0.009 |
| TTP % | NS | 0.426 | NS | 0.162 |

| DIRECTION | RIGHT ROTATION | | LEFT ROTATION | |
|---|---|---|---|---|
| | IMPAIRMENT PERCENTAGE | P VALUE | IMPAIRMENT PERCENTAGE | P VALUE |
| RESPONSE TIME (S) | NS | 0.330 | NS | 0.062 |
| MOVEMENT TIME (S) | 26 | <0.0001 | 40 | 0.001 |
| PEAK VELOCITY (°/S) | -38 | <0.0001 | -35 | <0.0001 |
| MEAN VELOCITY (°/S) | -28 | <0.0001 | -35 | <0.0001 |
| NO. VELOCITY PEAKS | 34 | 0.002 | 44 | 0.008 |
| TTP % | -30 | 0.017 | NS | 0.265 |

Figure 15

| OUTCOME MEASURE | MODEL SIG. | PREDICTOR SIG. | OPTIMAL PREDICTOR VALUE | SENSITIVITY | SPECIFICITY |
|---|---|---|---|---|---|
| NVP E | 0.02 | 0.0286 | 3.5 | 0.96 | 0.36 |
| VPEAK F | 0.0005 | 0.0033 | 89.63 | 0.88 | 0.67 |
| VPEAK LR | <0.0001 | 0.0005 | 143.02 | 0.84 | 0.65 |
| VMEAN LR | <0.0001 | <0.0001 | 47.15 | 0.80 | 0.83 |
| VMEAN E | <0.0001 | 0.0003 | 37.18 | 0.80 | 0.80 |
| VPEAK E | <0.0001 | 0.0003 | 93.95 | 0.76 | 0.81 |
| MT LR | <0.0001 | 0.003 | 1.33 | 0.76 | 0.65 |
| VPEAK RR | <0.0001 | 0.0004 | 112.89 | 0.68 | 0.83 |
| NVP RR | 0.0135 | 0.04 | 4.00 | 0.64 | 0.69 |
| VMEAN RR | 0.0002 | 0.0016 | 42.27 | 0.60 | 0.81 |
| VMEAN F | 0.002 | 0.006 | 26.02 | 0.60 | 0.74 |
| MT E | 0.0052 | 0.01 | 1.38 | 0.60 | 0.72 |
| TTP% LR | 0.03 | 0.04 | 63.06 | 0.56 | 0.74 |
| MT F | 0.0039 | 0.0117 | 1.32 | 0.52 | 0.88 |
| MT RR | 0.0029 | 0.0089 | 1.38 | 0.52 | 0.81 |
| NVP F | 0.0347 | 0.06 | 5.8 | 0.52 | 0.81 |
| NVP LR | 0.004 | 0.01 | 5.8 | 0.44 | 0.88 |

| OUTCOME MEASURE | ACCURACY | AREA UNDER CURVE | UNIT ODDS RATIO | ODDS RATIO 95% LOWER CL | ODDS RATIO 95% UPPER CL |
|---|---|---|---|---|---|
| NVP E | 0.32 | 0.65 | 1.36 | 1.03 | 1.78 |
| VPEAK F | 0.55 | 0.76 | 0.975 | 0.96 | 0.99 |
| VPEAK LR | 0.48 | 0.79 | 0.976 | 0.96 | 0.99 |
| VMEAN LR | 0.63 | 0.83 | 0.91 | 0.87 | 0.95 |
| VMEAN E | 0.59 | 0.81 | 0.91 | 0.87 | 0.96 |
| VPEAK E | 0.57 | 0.81 | 0.97 | 0.96 | 0.99 |
| MT LR | 0.40 | 0.77 | 14 | 2.45 | 79.98 |
| VPEAK RR | 0.51 | 0.81 | 0.974 | 0.96 | 0.99 |
| NVP RR | 0.33 | 0.67 | 1.44 | 1.02 | 2.05 |
| VMEAN RR | 0.41 | 0.75 | 0.938 | 0.90 | 0.98 |
| VMEAN F | 0.34 | 0.70 | 0.93 | 0.88 | 0.98 |
| MT E | 0.31 | 0.69 | 5.04 | 1.47 | 17.27 |
| TTP% LR | 0.30 | 0.64 | 0.95 | 0.90 | 1.00 |
| MT F | 0.40 | 0.74 | 7.34 | 1.56 | 34.62 |
| MT RR | 0.33 | 0.70 | 8.12 | 1.69 | 39.00 |
| NVP F | 0.33 | 0.67 | 1.323 | 0.99 | 1.77 |
| NVP LR | 0.32 | 0.69 | 1.37 | 1.07 | 1.76 |

MOTION ASSESSMENT SYSTEM AND METHOD

CROSS-REFERENCE TO RELATED APPLICATIONS

This application is a National Phase Application of PCT International Application No. PCT/IL2009/001135, International Filing Date Dec. 2, 2009, claiming priority of US Provisional Patent Applications, 61/119,397, filed Dec. 3, 2008, and 61/184,854, filed Jun. 8, 2009.

FIELD OF THE INVENTION

The present invention relates to medical analysis of movements and treatment of motion impairments. In particular, the invention relates to diagnostics of motion impairments and functional analysis of angular motions using surround displays.

BACKGROUND

Neck pain is a common musculoskeletal complaint with a reported annual prevalence ranging from 30% to 50%. Neck pain constitutes a major cause of disability in the western world with significant consequences for the injured individuals and for society at large. While disability due to neck pain entails various impairments such as reduced repositioning ability, diminished muscle activity and decreased isometric strength, limitation in cervical motion is the impairment most frequently clinically observed.

Cervical Range of Motion (CROM) assessment is frequently used to quantify the level of impairment associated with neck pain, to discriminate between asymptomatic persons and those with persistent neck pain related to different pathologies and to assess effectiveness of therapeutic interventions.

CROM assessment as a diagnostic tool is challenging due to previous studies that showed low specificity and sensitivity. A variety of means including eye-balling, radiographs, goniometers and inclinometers, as well as more advanced technologies such as ultrasonic, optic and electromagnetic motion tracking devices can be used.

Goniometers and inclinometers are used extensively for clinical purposes, but they are limited to measuring primarily two-dimensional motions under static conditions. Motion tracking devices may be used to measure three-dimensional motions under dynamic conditions, but their use is limited to research due to their cost and technical complexity.

CROM assessment is typically carried out by instructing subjects to move their head as far as possible in each of the tested planes of motion. However, the reliability of these assessment methods is questionable, as elicited conscious movements do not necessarily replicate typical functional movements which occur spontaneously in response to multiple natural stimuli. In daily life individuals turn their heads to maximal range unconsciously in response to hearing a sudden noise, or when attempting to perform actions such as driving a car in reverse or locating an attractive scent.

U.S. Pat. No. 6,613,003 titled "Test apparatus for determining a cervical acceleration injury" to "Hollandse Exploitatie MIJ BV" describes a system to evaluate vestibular deficits, claimed to be associated with whiplash. With this apparatus, normal environment is manipulated and there is no active involvement of the patient—thus no everyday function is assessed. Moreover, it does not measure mobility of the cervical spine or the quality of the motion (in terms of speed or smoothness) and is relevant only to a sub-group of whiplash patients who complain of vestibular problems such as dizziness.

In their paper on manual therapy titled "Sensorimotor disturbances in chronic neck pain—Range of motion, peak velocity, smoothness of movement, and repositioning acuity" Sjolander P et al. describe an evaluation of sensorimotor function in patients with chronic neck pain in comparison to the healthy subjects (Sjolander P, Michaelson P, Jaric S and Djupsjoebacker M, Manual Therapy, Volume 13, Issue 2, Pages 122-131). It is noted that Sjolander P et al. provide an analysis of cervical motions which are elicited by oral commands International Patent Application, publication number WO 2004/043,257 titled "Device for the diagnosis and/or therapy of functional disorders of the cervical spine" to Fraunhofer Ges Forschung et al describes a device used for tracking cervical motion. However these devices do not stimulate user reaction to unexpected targets which is a typical real-life scenario.

International Patent Application, publication number WO 9115148 titled "Non-invasive method of and equipment for determining kinematic movement of the cervical spine" to Fuhr Arlan W also describes equipment targeted towards assessment of cervical motion. The equipment described uses a flat display, thus limiting the angular cervical motion potential of the subject. In addition, the system is not adaptive to the specific subject's ability as displayed during the assessment session.

International Patent Application, publication number WO 02089923 titled "Apparatus for cervical region diagnostics and training" to Physiotech Aps describes a device where patients are requested to place their head inside the apparatus. Replication of a person's spontaneous posture cannot be achieved under such conditions.

U.S. Pat. No. 6,774,885 titled "System for dynamic registration, evaluation, and correction of functional human behavior" to Motek B V describes a system that uses virtual environments for assessment of global body motions and postural changes, and has interesting applications in the field of rehabilitation. This system, however, does not measure the neck and its kinematics. It is a whole body training system, which is targeted mostly towards achieving posture and balance.

The need remains, therefore, for an affordable system and methodology to assess cervical motion while simulating real life scenarios. Moreover, there's a need for similar systems and methods to assess linear and angular functional motion parameters of different body parts in human and non-human subjects.

Embodiments described hereinbelow address this need.

SUMMARY OF THE EMBODIMENTS

Embodiments described herein disclose a motion assessment system configured to monitor and analyze voluntary movements of a subject, comprising a surround-display configured to stimulate movement of the subject, a motion tracker configured to monitor the movements of the subject, and a processor configured to receive data from the motion tracker and to control the surround-display.

Optionally the system further comprises a data storage unit configured to store data received from the motion tracker. The connectivity between the motion tracker and the processor can be achieved through a wire, or it can be wireless. Optionally, the surround display is head mounted.

Optionally, the surround display comprises at least one of a visual output, an audio output and a tactile output. Optionally, the surround display is configured to block the subject from recognizing peripheral events happening outside the surround display.

Optionally, the motion tracking device is configured to track linear, rotational and angular movements.

Optionally, the processor is used to adjust the surround display according to input received from the tracking device. Optionally, the processor adjusts the surround display according to the learning curve of the subject. Optionally, the processor further uses a scaling factor to manipulate images appearing on the surround display.

Optionally, the system can further serve for training and exercise. Optionally, the system can be used in a therapeutic program for the treatment of motion impairments.

Other embodiments teach a method wherein movement of a subject is stimulated using a surround display, and the movement is monitored using a motion tracker. The method may further comprise the steps of setting failure criteria and ending the procedure of stimulating and monitoring the movements of the subject. The method may also comprise a preliminary step of determining an initial movement-range for the subject. The procedure may include stimulating the subject to perform movements within a desired movement-range.

The preliminary step of determining a desired-movement-range for the subject may comprise the substeps of conducting an initial assessment of the subject to determine an initial-movement-range and selecting a desired-movement-range within the initial-movement-range.

The method may further comprise the additional steps of assessing the subject's facility to perform the movements, adjusting the desired-movement-range in response to the subject's facility to perform the movements, and returning to the step where the movement of a subject is stimulated using a surround display.

Embodiments of the system and method may relate to voluntary movements of the neck, knees, eyes, back, ankles and shoulders. The movement parameters that can be tracked by embodiments of the system and method disclosed below are selected from a group consisting of fluency, smoothness, accuracy, velocity, acceleration, jerk, number of velocity peaks, range and force.

BRIEF DESCRIPTION OF THE FIGURES

For a better understanding of the invention and to show how it may be carried into effect, reference will now be made, purely by way of example, to the accompanying drawings.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention; the description taken with the drawing making apparent to those skilled in the art how the several forms of the invention may be embodied in practice.

Figure 1:
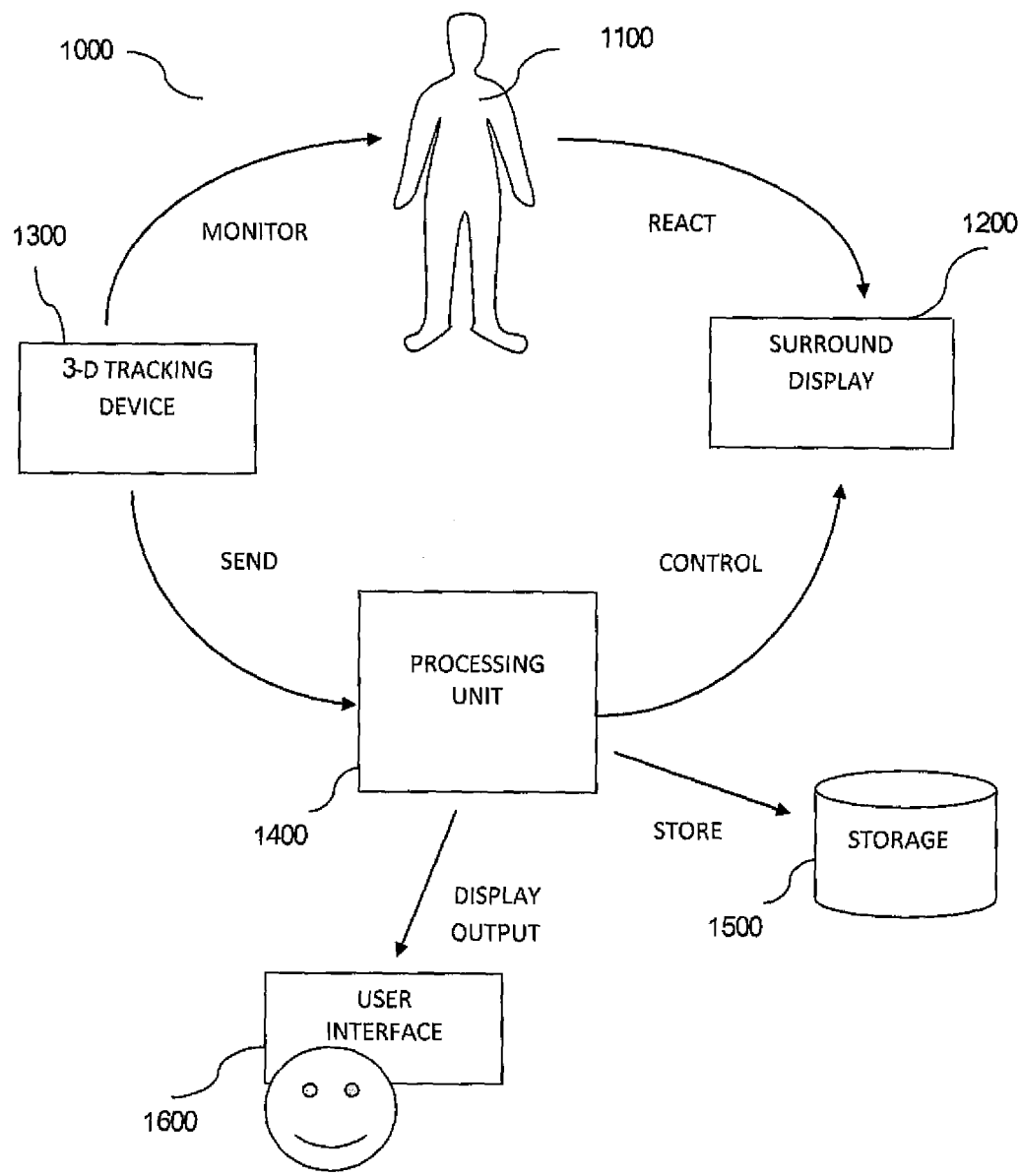
Figure 2:
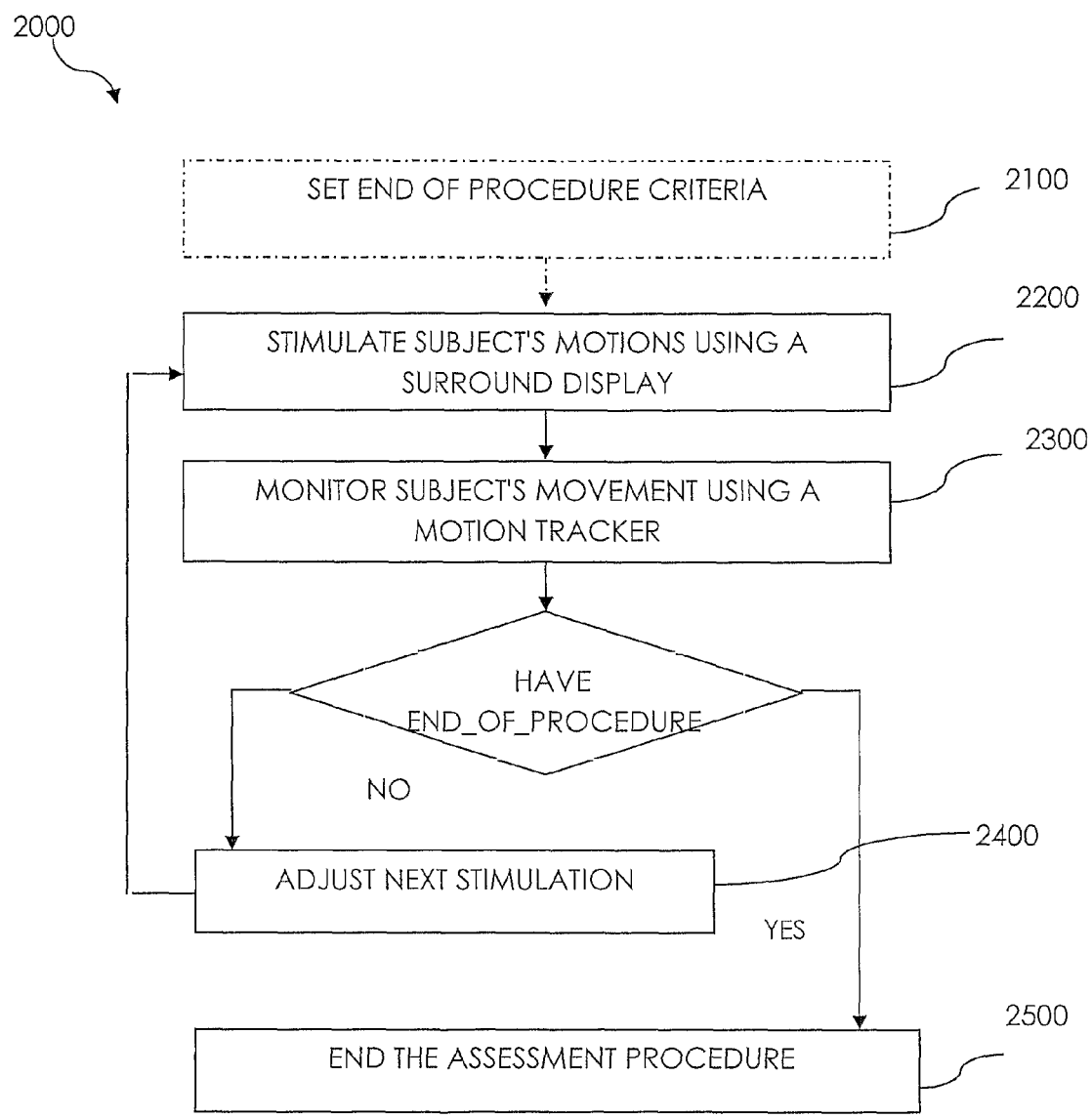
Figure 3:
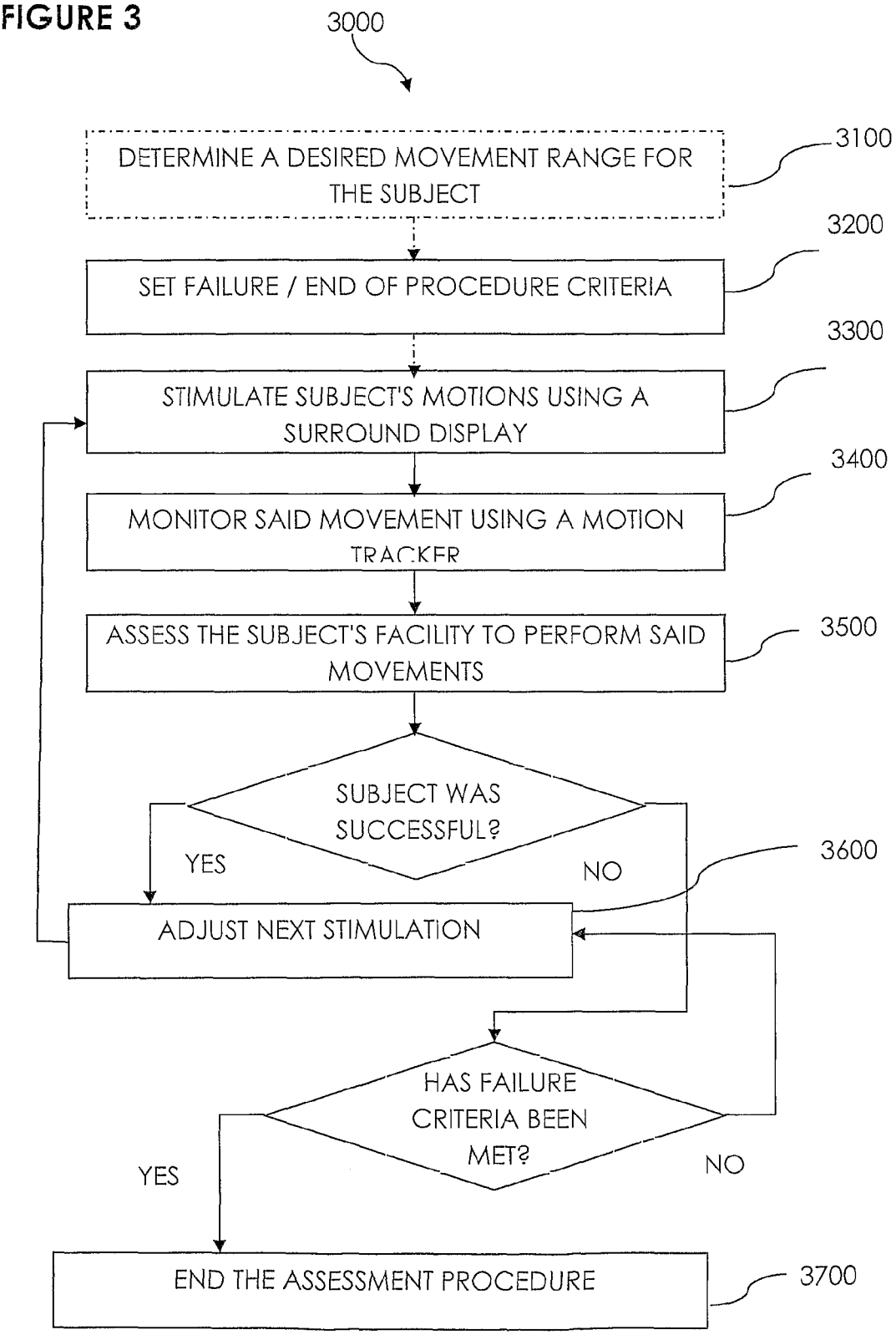
Figure 4:
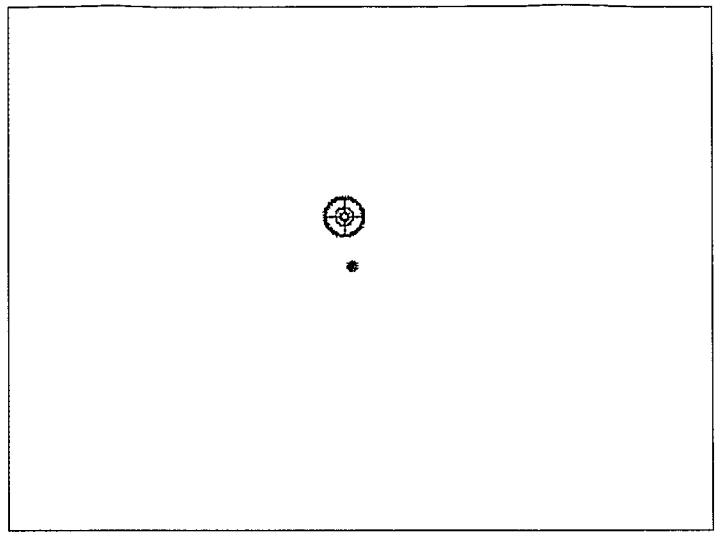
Figure 5:
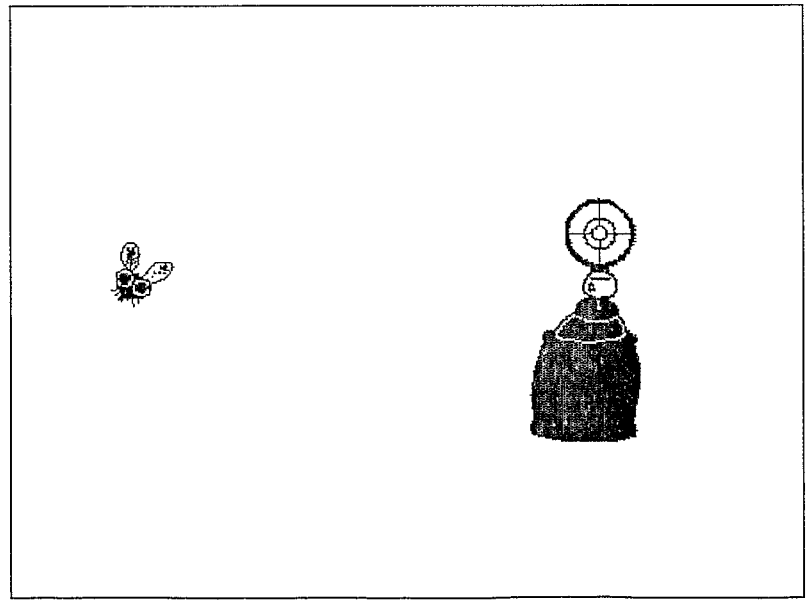
Figure 7:
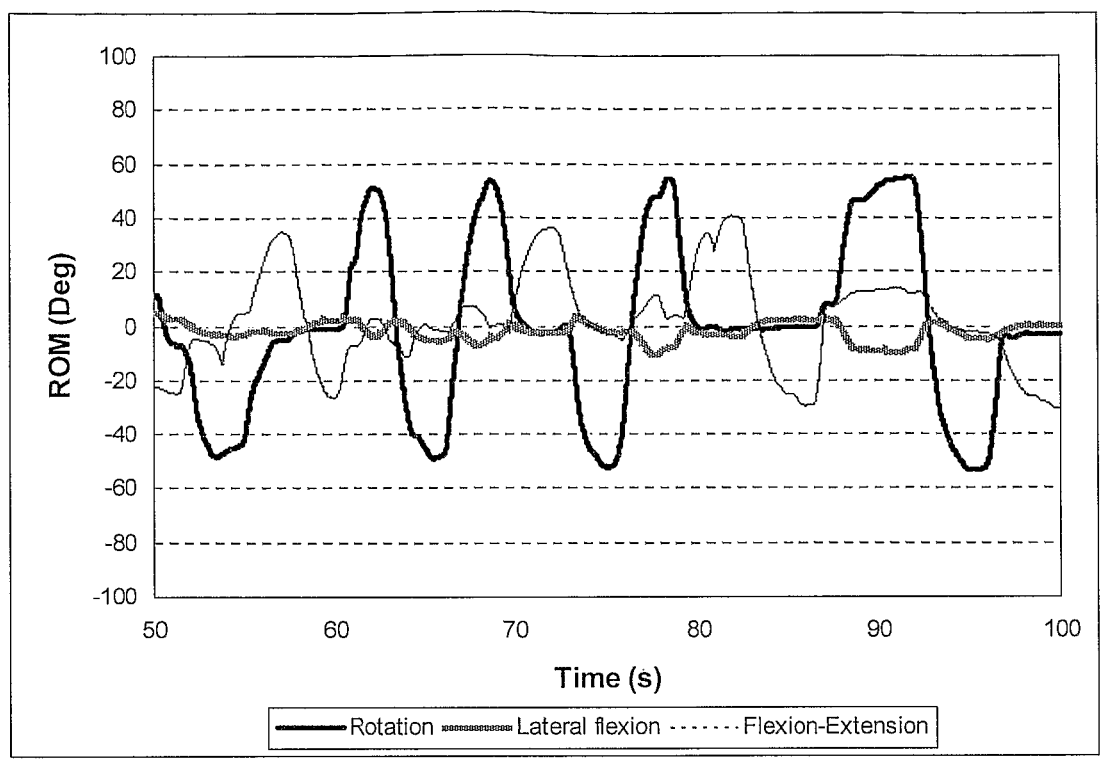
Figure 8:
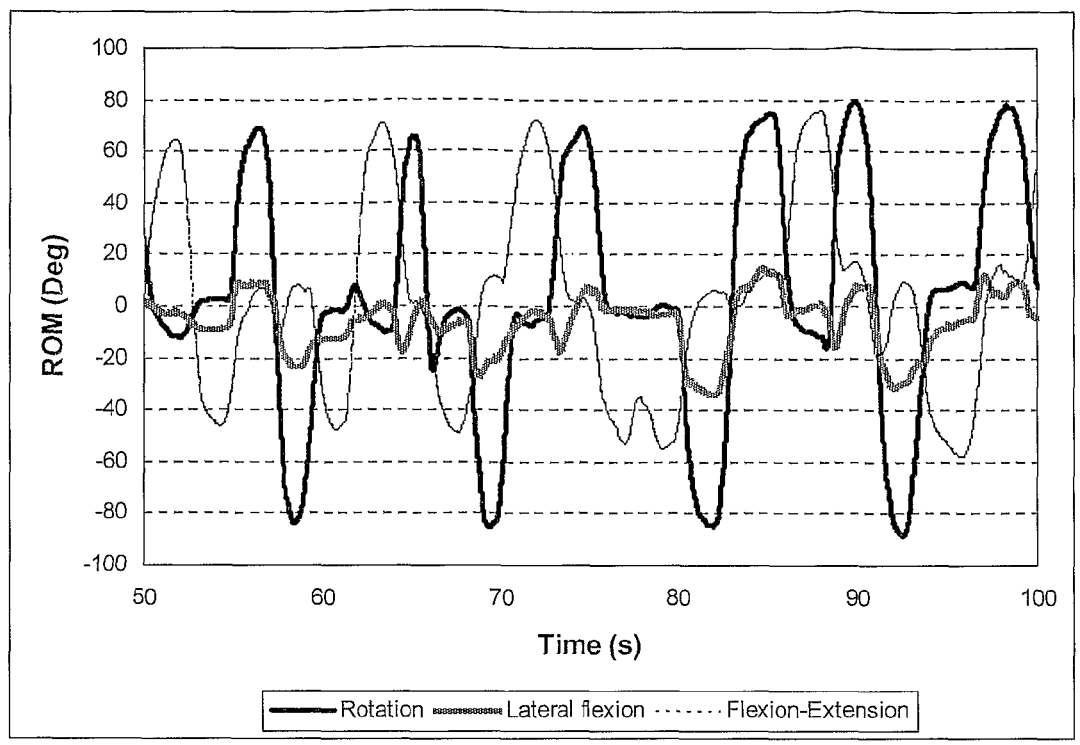
Figure 10:
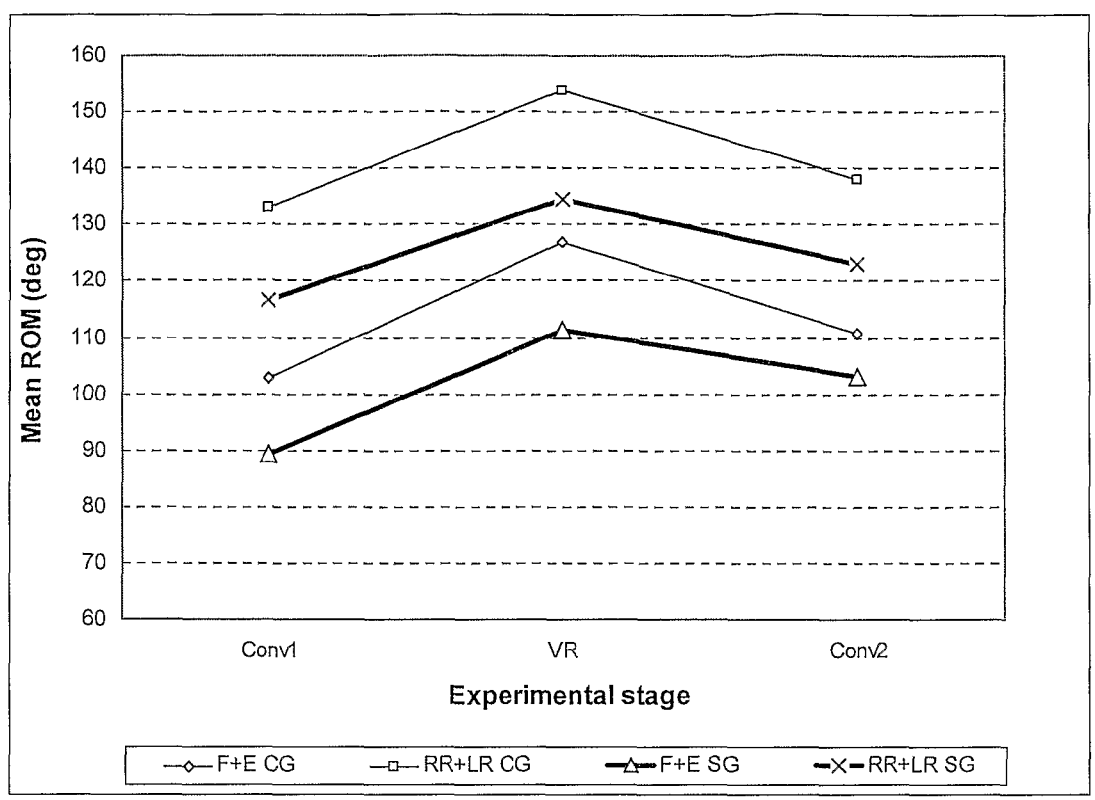
Figure 12:
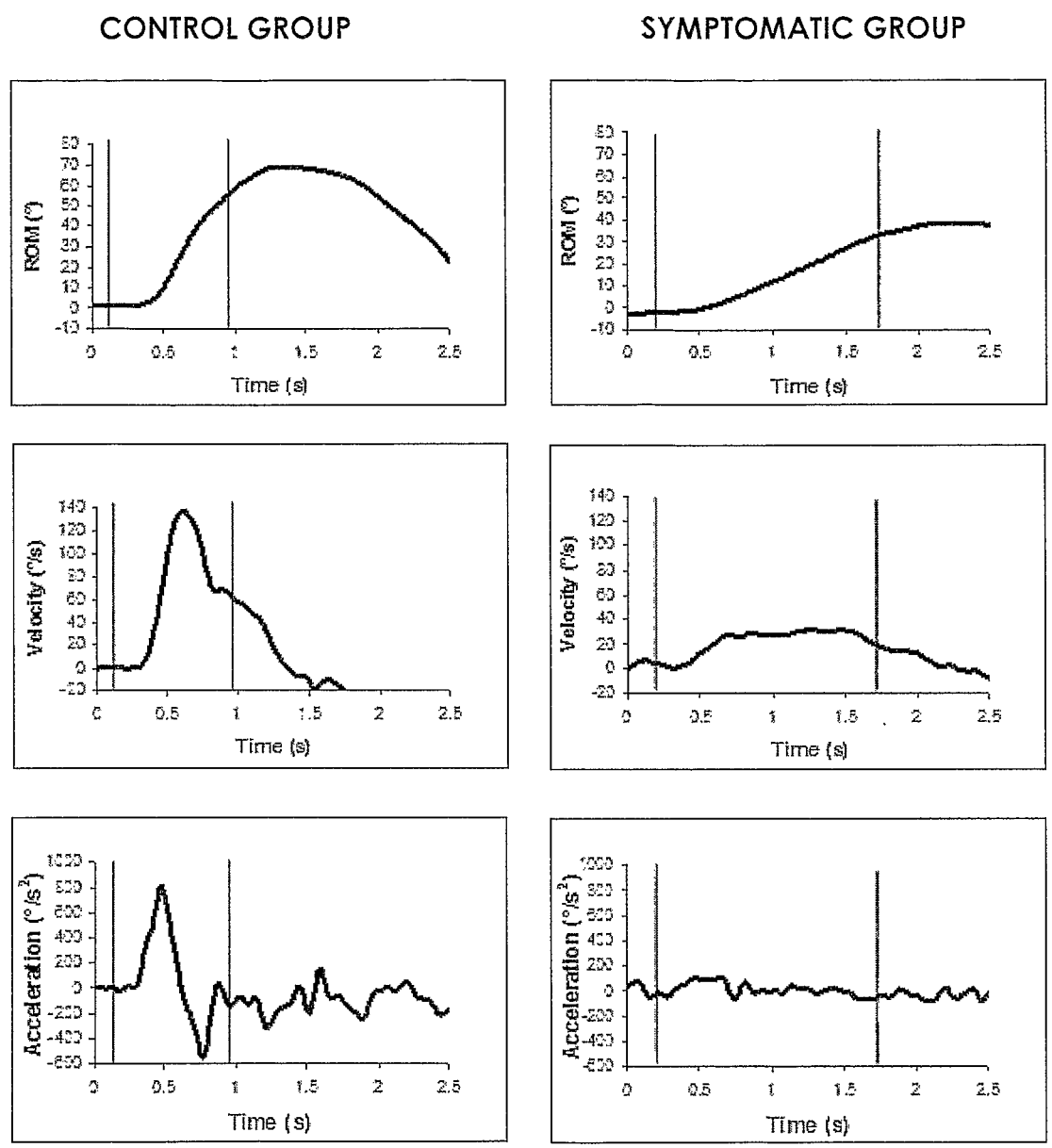

In the accompanying drawings,

FIG. 1 is a schematic block diagram representing the main components of an embodiment of a motion assessment system;

FIG. 2 is a flowchart showing the basic steps of the motion assessment method;

FIG. 3 is a flowchart showing a more detailed flow of the motion assessment method, and FIGS. 4-15 refer to a study done on a specific cervical embodiment of the motion assessment system and method. In these figures:

FIG. 4 illustrates a screen capture from the beginning of a VR game, showing a red dot on the middle of the screen, and a target sign, representing the participant's head location, FIG. 5 illustrates a screen capture from the VR game, showing a fly-target appearing on the left hand side, and the spray canister with the target sign, representing the participant's head location, the participant's task being to move the spray canister to the fly;

FIG. 6 illustrates the characteristics of a symptomatic group and a control group;

FIG. 7 illustrates a motion trajectory of a symptomatic patient as elicited and measured by the cervical embodiment of the motion assessment system;

FIG. 8 illustrates a motion trajectory of a control subject as elicited and measured by the cervical embodiment of the motion assessment system;

FIG. 9 illustrates a range of motion means and standard deviations at different stages of the assessment as measured in the symptomatic group and the control group;

FIG. 10 illustrates the mean cervical range of motion, as maintained in the three experimental stages, by the symptomatic group and the control group;

FIG. 11 illustrates a diagnostic value of significant outcome measures;

FIG. 12 illustrates angular displacement, velocity and acceleration profiles of an asymptomatic subject (left) and a symptomatic subject (right) during movement to a target eliciting right rotation;

FIG. 13 illustrates the mean and standard deviation values of kinematics measures;

FIG. 14 illustrates the differences between groups in each outcome measures, and FIG. 15 illustrates diagnostic value of significant outcome measures.

DETAILED DESCRIPTION OF THE SELECTED EMBODIMENTS

Embodiments of the present invention disclose systems which stimulate voluntary body movements and measures motion-related parameters. Such systems can be used for assessing mobility capabilities or serve as a therapeutic tool for training and exercise. It can readily be applied to subjects even if they are less cooperative with traditional assessment methods, such as subjects suspected of insurance fraud, children, infants or the like.

Embodiments may be used in assessing different kinematic parameters of motion analysis including but not limited to range, velocity, acceleration, jerk, number of velocity peaks, fluency, smoothness, accuracy, response time, time to peak velocity ratio and the like.

Reference is now made to the block diagram of FIG. 1, showing the main components of an embodiment of the system 1000 and how they interact. The system may include a surround display 200, a tracking device 300, a processing unit 400 and optionally a storage unit 500 and a user interface 600 to be used by the person conducting the assessment.

It is a particular feature of embodiments of the display 200 that it is placed in a manner that surrounds the subject 100 and blocking peripheral distractions and preventing the subject 100 from noticing events happening outside the display. The subject 100 reacts to the events happening on the display 200.

The tracking device 300 typically includes sensors which may be placed about the subject 100 in strategic points. The tracking device 300 monitors the movements of the subject 100, and sends information regarding these movements to the processor 400. The processor 400 is configured to analyze the information received from the tracking unit 300, and to control the events that appear on the display 200. The processor 400 may optionally be further configured to display data to the user interface 600. In addition, the storage unit 500 may be provided and the processor 400 may be configured to store data therein.

Using visual, auditory, tactile or haptic inputs, the display environment is designed to stimulate and encourage the subjects to perform specific motions while their attention is focused on the display. Objects appearing on the display facilitate spontaneous motion throughout the assessment session. This is done to simulate real life scenarios, for objective assessment of motion-related parameters.

The subjects' movements may be monitored by the tracking unit 300 and analyzed by the processor 400. The analysis results are used to determine what the content of the display 200 will be. Hence, a complete cycle may be formed: the subjects' movements stimulated by the display also serve as input which will be analyzed and used to control what will be displayed in the future.

FIG. 2 illustrates a possible process for motion assessment using embodiments of the system. The process 2000 consists of the basic steps of stimulating subject's motions using a surround display 2200 and monitoring the subject's movements using a motion tracker 2300. Typically these steps are repeated in a loop until some end-of-procedure criteria are met which may be set in a preliminary step 2100. If the end-of-procedure criteria decided upon in step 2100 have not been met, the next stimulation is typically adjusted 2400 and the process repeats step 2200 with the new stimulation. Once the end-of-procedure criteria have been met, the procedure ends 2500.

FIG. 3 illustrates a second possible process, where the end-of-procedure criteria are determined according to the extent of the subject's success in performing the required tasks. The process optionally commences with determining the desired movement range of the subject 3100. This can be achieved by conducting an initial assessment, possibly using systems and methodologies known in the art. Setting the end-of-procedure criteria 3200 may be determined according to the number or extent of subject's failures in performing certain movements. Each stimulation of the subject's motions using a surround display 3300 and monitoring the subject's movements using a motion tracker 3400, is followed by an assessment of the subject's success in performing the desired movement 3500. Adjusting the next stimulation 3600 is done in accordance with the assessment results of step 3500, and the process returns to step 3300. This continues until the end-of-procedure criteria have been met—in which case, the assessment is ended 3700. For example, end-of-procedure criteria may determine that the assessment is ended after the subject fails to perform the desired motion, say, three times consecutively, within a given time limit, absolutely or such like. Various embodiments of the motion monitoring system may be configured to monitor different body parts including, for example and without limitation, the neck, lower back, shoulders, knees, ankles and other joints, as well as eyes and other movable body parts. Optionally, systems may be configured to provide diagnosis of mobility impairments and pain assessment.

Accordingly, amongst others, embodiments may be provided for the following applications.

a. Diagnosis or treatment of cervical motion

Suitable embodiments may include a tracking device comprising sensors placed on the head and sternal notch, and a display presenting an interactive video game including tasks stimulating linear and angular movements of the neck.

b. Diagnosis or treatment of low back pain

Suitable embodiments may include a tracking device comprising sensors on the pelvis and lumbar spine, and a display presenting an interactive video game including tasks stimulating lumbar motion (for example, bending under a bridge, limbo dancing or such like).

c. Diagnosis or treatment of shoulder pain

Suitable embodiments may include a tracking device comprising sensors on arm, hand and trunk, and a display presenting an interactive video game including tasks stimulating oriented at hand motion and precision (reaching and touching visual targets or such like).

d. Diagnosis or treatment of knee pain

Suitable embodiments may include a tracking device comprising sensors on patella, femur and tibia, and a display presenting an interactive video game including tasks stimulating tasks oriented at leg motion and precision (kicking a football or such like).

e. Diagnosis or treatment of ankle pain

Suitable embodiments may include a tracking device comprising sensors on tibia, fibula and foot, and a display presenting an interactive video game including tasks stimulating ankle motion and precision (raising heel or toes or such like).

f. Diagnosis or treatment of ocular motor control

Suitable embodiments may include a tracking device which uses dark and bright pupil tracking techniques, and a display presenting interesting events which stimulate specific eye movements. Embodiments of such system may stimulate and track each eye separately or both eyes together.

It is noted that according to various embodiments the motion monitoring system may be further configured to train body parts to perform desired movements. Training performed with embodiments of this system may be used for treatment of injured body parts as well as exercising and strengthening targeted body parts of healthy subjects. Targeted body parts may include, for example and without limitation, the neck, lower back, shoulders, knees, ankles and other joints, as well as eyes and other movable body parts.

It will be appreciated that training body parts using embodiments of the system may be particularly useful for sports training to monitor and enhance athletic performance. For example the system may be used to train a targeted body part to improve mobility parameters such as reaction time, agility, muscle strength, range of motion and the like.

Cervical Motion Embodiment—System and Procedure

The specific cervical motion embodiment presented below discloses a Virtual Reality (VR) environment as a display in which an electromagnetic tracking system is used to monitor Cervical Motion parameters as subjects are involved in a simple and engaging gaming scenario.

The cervical motion embodiment proved successful in revealing that kinematic measures, such as velocity or smoothness of motion, are significant diagnosing factors of neck pain. It can provide exact measures to subjects' functional performance of neck motion, quantify subjects' limitations, and enable accurate differentiation between symptomatic and healthy subjects.

Using visual and auditory input, the virtual environment is designed to motivate the participants to move their head to maximal range while their attention is focused on playing a challenging game. In this specific embodiment, visual targets facilitate spontaneous cervical motion throughout the game to simulate real life scenarios that require cervical mobility. Determination of targets' location and an unbiased measuring device are used for objective assessment of neck impairment.

The cervical motion assessment embodiment can also be used for treatment purposes, such as to improve functional performance of cervical motion in patients suffering from neck pain in a motivating and engaging procedure. Other embodiments including a suitable display and a mobile tracking system may also be used for this purpose. The patient can run his exercise program on his personal computer. A specific exercise program may be tailored for each patient according to his ability and limitations, as diagnosed in the assessment.

Cervical motion assessment using VR environment includes components that make it hard to deceive. The motivating environment, the immersion effect of the virtual reality environment and the random stimulations distract subjects from potential pain associated with these motions. User distraction and accurate measuring means may create a more valid method of assessment.

Active interaction within a VR environment enhances the effectiveness of exercise interventions in various patient populations, and also ameliorates pain and anxiety experienced in various settings. These attributes of the VR technology may serve well in the assessment and rehabilitation of individuals with limited CROM due to pain.

Cervical motion assessment embodiments may integrate use of electromagnetic tracking with a Head Mounted Display (HMD). Real-time cervical motion tracking controls user interaction in the video game projected in the HMD.

The HMD unit for example I-glasses HRV Pro, Virtual Realities, may be adjusted and strapped to the participant's head. The electromagnetic tracking system such as the systems provided by Ascension™ or Polhemus™, for example, may be used to capture cervical motion in real time with six degrees of freedom (x, y and z coordinates and rotations). Two sensors are typically used, one placed centrally at the back of the HMD and the second placed on the sternal notch allowing the isolation of cervical movement from trunk motion. Other tracking devices may be used, for example and without limitation accelerometers, gyroscopes, optical tracking devices and the like. Management of the tracking output data may be processed using suitable software such as Matlab™ software or the like.

According to a selected embodiment, the VR environment may be a customized video game displayed via the HMD unit, and presents targets randomly appearing in four directions, eliciting cervical extension (E), flexion (F), right rotation (RR), and left rotation (LR). Participants' task is to align a VR cursor with the target that appears on the HMD unit. The subject's cervical motions control the location of the cursor upon the display. Once alignment between the target and the cursor is achieved, the target vanishes. A new target may then appear, typically requiring larger Range of Motion (ROM). Usefully the cursor may appear as an icon indicative of a direction for example a gun-sight, gun barrel, sports bat, spray canister nozzle, steering wheel or the like as commonly used in gaming.

It is a particular feature of the cervical motion assessment embodiment that the location of the new target may appear to the subject as being similar or even identical to the location of the previous target, but in fact may require a larger range of motion. This may be achieved by altering a scaling factor affecting screen proportions and the appearance of objects on the screen. The scaling factor may further affect the extent to which a given movement of the subject effects the movement of the cursor. For example, during the initial presentation of the target, to move the cursor across its full range may require the subject to move a joint through, say, a 30 degree angle or so. As the subject successfully performs the tasks set, the scaling factor may be adjusted such that a larger angle may be required to move the cursor across its full range. Similarly, where required, the scaling factor may be adjusted such that a smaller angle may be required to move the cursor across its full range. Typically, throughout the VR gaming, motion may be continuous between targets with no return to a stationary mid-position, or interrupted by a request to return to a stationary position.

Reference is now made to FIGS. 4 and 5, showing projected screenshots of an embodiment of the VR program. In this embodiment, targets appear in the shape of flies, and the subjects' task is to "spray" each fly by aligning a spray canister icon therewith. Cervical motions control the location of the canister nozzle. Once the fly is sprayed, it vanishes and a new target appears, typically requiring a larger ROM.

The procedure for assessing CROM with the system may be carried out as participants sit on a standard firm chair, typically with their body strapped by a seat-belt and their feet resting on the ground. Each VR session may commence with a short warm-up and introductory explanation of the virtual game. The start point for the VR game is generally set at 80% of the maximal cervical range displayed by the subject using conventional assessment techniques.

The procedure may continue with targets being displayed on the HMD and the subject's cervical movements being monitored and analyzed. The selection of targets appearing on the display may be adjusted according to the performance of the subject. Typically, the process repeats until the user fails to increase his CROM a predetermined number of times and no CROM improvement is recorded.

FIGS. 6-15 illustrate an extensive study performed using the cervical assessment embodiment illustrated above. The study used the VR system and method described in this invention alongside with other assessment methods and compared the assessment results received from both. This study evaluated the reliability and validity of the specific embodiment of the cervical assessment system and method illustrated above, by performing a. a reliability study; b. a comparative study which demonstrated differentiating ability of the system; c. a comparison to existing conventional method, with results showing VR is advantageous; and d. an analysis of diagnostic ability using logistic regression.

CROM measures included both half-cycle Extension (E), Flexion (F), Left Rotation (LR), Right Rotation (RR), left lateral flexion (LLF), and right lateral flexion (RLF) and full-cycle (F+E, RR+LR, RLF+LLF) cervical ROM. The primary ROM results collected by the system described in this invention were full cycle F+E, and RR+LR, as VR motion was continuous between targets, with no return to a middle point. Mid-position was recorded at the beginning of the experiment and used to calculate half-cycle measures.

The study simulated three sessions, where only the second session (VR) used an embodiment of the system and method described hereinabove to trigger cervical motion. The other two sessions (Conv1 and Conv2) included voluntary cervical motion in response to oral commands. Participants were requested to move their head twice into E, F, LR, RR, LLF and RLF. The measurement system used in all 3 sessions was identical.

Results obtained from both VR and conventional assessments demonstrated significantly reduced range of motion in the symptomatic group. In addition, logistic regression analysis, using a single predictor, compared the ability of conventional versus virtual tests of cervical ROM to distinguish between symptomatic and asymptomatic individuals. The VR measures showed greater sensitivity while conventional measures showed greater specificity. Results also showed that exposure to a single session using the VR system caused a significant increase in ROM.

The symptomatic group included 25 volunteers (16 females and 9 males, mean age $\pm SD=39.0\pm12.7$ years) presenting with chronic neck pain from an outpatient physiotherapy clinic and from the University of Haifa. The control group included 42 asymptomatic volunteers (31 females and 11 males, mean age $\pm SD=35.3\pm12.4$ years) recruited from the University of Haifa. Inclusion criteria for the symptomatic group included neck pain with or without pain to the upper limb for longer than six weeks.

Exclusion criteria for both groups were report of neurological, metabolic, visual or vestibular disorders, significant internal pathology which may affect the spine (e.g., ankylosing spondylitis, rheumatic conditions, scoliosis), chronic intake of drugs which may alter pain or performance e.g. steroids, non-steroidal-anti-inflammatory-drugs, and dizziness complaints present at the time of the experiment. Additional exclusion criterion for the control group alone included previous history of neck/spinal trauma or pathology.

A Visual Analogue Scale (VAS) of 100 mm line was used to document pain intensity reported at the beginning of the assessment. The Tampa scale of kinesiophobia (TSK) was used to assess fear of movement or re-injury, and reported a cut-off score of 39.

All 67 participants were assessed by the same assessor. Each cervical motion assessment took approximately 20 minutes, with an addition of 10-15 minutes for symptomatic participants. The experimental session commenced with an interview regarding possible exclusion criteria, history, and a description of symptoms when applicable. Participants presenting with neck pain then filled in the NDI questionnaire, the VAS for pain intensity and the TSK questionnaire.

The mean value of 2-3 largest ROM results to each direction was used for statistical analysis. Differences between results of the two groups (controls vs. symptomatic), the two planes of motion (sagittal vs. horizontal), and the three stages (Conv1, VR, and Conv2) were assessed by a mixed-model ANOVA for full cycle and half cycle measures. When the ANOVA indicated significant overall differences between stages, pairwise stage differences were assessed by the Tukey test.

Univariate and multivariate logistic regression analyses and receiver operating characteristic (ROC) curves were used to examine the predictive relationship between test parameters and status (symptomatic vs. control groups). In addition to tests of model significance and ROC area under the curve (AUC), these analyses included determination of odds ratios and their confidence intervals, and sensitivity and specificity of different model cut-off thresholds. Significance was determined at $p \leq 0.05$. JMP® statistics software was used (S.A.S Institute), as well as SAS® software (Statistical Analysis Software).

Reference is now made to FIG. 6 illustrating characteristics of the symptomatic (patients) group and the control group. Results were obtained from 67 participants who were assessed by the conventional and VR methods. Comparable demographic baseline values for control and symptomatic groups were found with no significant differences in age or in gender (p>0.1). Characteristics of the symptomatic group are listed including etiology, duration, symptomatic side, pain intensity, functional disability, and kinesiophobia levels. The majority reported duration of symptoms as very chronic, with neck pain lasting for a mean of 3.5 years (SD=4.5).

Seven (28%) out of the 25 symptomatic subjects reported an etiology of whiplash injury, and remaining 18 (72%) experienced an atraumatic, insidious onset of symptoms. Eighteen (72%) symptomatic subjects reported unilateral symptoms, and seven (28%) reported their symptoms to be bilateral or central (table 1). The mean severity of pain and functional disability, as indicated by the VAS and NDI scores, was mild. The mean level of kinesiophobia as measured by the TSK was just below the cut-off score (39) identified as associated with risk of prolonged pain related disability.

Reference is now made to FIGS. 7 and 8 illustrating a motion trajectory of a symptomatic patient in virtual reality and a motion trajectory of a control subject in virtual reality, respectively. Examples of 3D cervical motion trajectories during the VR session of one symptomatic and one control subject are presented. The ROM increased for both participants as the game proceeded, although the values for the symptomatic participant are considerably smaller than that of the control subject.

Reference is now made to FIG. 9 illustrating a range of motion means and standard deviations at each stage for the control group and for the symptomatic group. The table lists the mean and SD of cervical ROM measures (in degrees) collected from both control and symptomatic groups in the three experimental stages (Conv1, VR, Conv2). A mixed-model ANOVA (group, experimental stage, plane of motion) for full-cycle ROM measures indicated significant overall differences (a) between groups ($F(1,65.3)=15.2$, $p=0.0002$), (b) between experimental stages ($F(2,296)=121$, $p<0.0001$), and (c) between sagittal and horizontal planes of motion ($F(1,294)=487.6$, $p<0.0001$). All interactions were non-significant (p>0.1) with one trend found in the interaction between plane and group (p=0.06).

Reference is now made to FIG. 10 illustrating a mean cervical range of motion, as maintained in the three experimental stages. The lack of significant interactions is illustrated by the parallel lines in the figure.

Reference is now made to FIG. 11 illustrating diagnostic values of significant outcome measures. Diagnostic values are sorted by sensitivity, from highest to lowest. This format of presentation demonstrates clearly that high sensitivity was found for VR F+E (88%), and good sensitivity (72%) was found for VR RR+LR; In contrast, conventional ROM measures demonstrated poor sensitivity (<60%) but had specificity values that were higher than VR measures, showing high specificity of 88%, i.e. 37 out of 42 control subjects were identified correctly using conventional measures.

Reference is now made to FIG. 12 illustrating angular displacement, velocity and acceleration profiles of an asymptomatic subject (left) and a symptomatic subject (right) during movement to a target eliciting right rotation.

Kinematic measures were collected from the two sensors for each of the 16 assessment trials throughout the virtual game. Each trial was defined from target appearance to target hit. Mean values of each of the kinematic outcome measures were calculated for each of the four directions (F, E, RR, LR), for each participant. The data were low pass filtered at Hz and a velocity profile was computed for each trial, using angular rotations in all three planes, (trunk rotations were subtracted from head rotations).

The following kinematic measures were analyzed during the trial:

Movement time is defined as the time from initiation of motion to hit of target.

Response time was defined from target appearance to motion initiation. Response time is shown as the distance between the first vertical line and first arrow.

Peak velocity (Vpeak) is the maximal velocity value recorded throughout a trial. The time at which Vpeak appeared is shown by the second arrow.

Mean velocity (Vmean) is the mean value of velocity throughout a trial.

Time to peak (TTP) is the time from motion initiation to peak velocity moment, in percentage out of total movement time. TTP is shown as the distance between the two arrows.

Number of velocity peaks (Vpeaks No.) is the number of velocity peaks from motion initiation to hit. Vpeak No. was defined by counting the number of times that the acceleration curve changed polarity, i.e., crossed the zero line. Vpeaks no. is a measure representing fluency of motion, i.e. the more velocity peaks in a motion the jerkier it is.

Range of motion (ROM) was collected in the initial phase of the VR game, and was discussed previously.

The experimental session commenced with an interview regarding possible exclusion criteria, and the completion of the VAS, NDI and TSK questionnaires by the symptomatic participants. The assessor was an experienced physiotherapist who performed all assessments. Cervical VR assessments were carried out in the sitting position, with the trunk strapped by a seat-belt, and feet resting on the ground. A short warm-up and introductory explanation of the virtual game was conducted prior to assessment. This was followed by a short conventional ROM assessment in which cervical ROM was tracked while subjects responded to an oral command to move the head twice into full ROM in all directions. This measurement was utilized for determination of VR targets location. Assessment with the VR tool followed, including the initial ROM phase1, and the second velocity phase, presented here. VR assessments were performed on all 42 asymptomatic participants and 25 symptomatic participants. No significant differences in age or gender were found between the control and symptomatic groups (p>0.1), supporting their baseline comparability. The majority of the symptomatic participants were very chronic, with a mean±SD duration of symptoms=3.5±4.5 years. Clinical results indicated mild severity, with a mean VAS score of 3.3±2.05, and mild disability, with a mean NDI score of 11.60±4.88. A moderate level of fear of motion was found, with a mean TSK score of 35.74±5.71, which was just below the threshold identified as associated with the risk of prolonged pain related disability.

Examples of VR trials in right rotation motion, of one symptomatic and one control subject are presented in the figure. The vertical lines in the figure indicate the limits of the trial, from target appearance to target hit. This example demonstrates that the symptomatic participant spent considerably more time moving towards the target than did the asymptomatic participant, as indicated by the time elapsed between the vertical lines. ROM was smaller for the symptomatic participant as target location was determined according to one's ROM, evaluated during the initial phase of the experiment. In the velocity profile, not only the amplitude (representing Vmax) is reduced for the symptomatic participant, but there is no one clear velocity peak, rather a staggered, slow drift to target. The time elapsed from motion initiation (first arrow in the figure), to peak velocity (second arrow in the figure) is longer for the symptomatic individual compared to the asymptomatic individual. The relationship between the velocity and acceleration profiles shown in the figure presents (a) similar behavior of velocity and acceleration in motion initiation, with a sharp increase in both simultaneously; (b) whenever the acceleration curve changed sigh (crossed zero line) a velocity peak was recorded; and (c) the example from the control group shows a smooth velocity profile, with one primary peak and a secondary small peak. However, the symptomatic individual presented with a very jerky velocity and acceleration profiles, with multiple velocity peaks throughout the trial.

Reference is now made to FIGS. 13 and 14 illustrating means and standard deviation of kinematics measures and difference between groups in each outcome measures, respectively. Mean and SD values for all kinematic measures of both groups are presented in FIG. 13. P values from the non-paired t-test performed are presented in FIG. 14 for all outcome measures. Additionally, FIG. 14 presents group difference in percentage, indicating the proportion of the difference between groups out of the asymptomatic mean result.

Significant differences between groups were found in all motion directions for movement time ($p<0.005$), peak velocity ($p<0.0001$), mean velocity ($p=0.001$ for F, and $p<0.0001$ for E, RR, and LR), and number of velocity peaks ($p=0.018$ for F, and $p<0.01$ for E, RR, and LR). Therefore, participants presenting with neck pain showed slower and jerkier cervical motion during motion towards virtual targets, compared to control subjects. However, no significant group difference ($p>0.05$) was found for response time, and for time to peak (TTP), with the exclusion of TTP in RR which showed significant difference ($p=0.017$).

As shown in FIG. 14, peak velocity was most limited in extension-directed cervical motion with a 41.2% relative reduction due to neck pain, followed by RR (38.3%), LR (34.6%), and flexion (33.5%). Similarly to findings in peak velocity, mean velocity was most limited in extension, with a 37.5% relative reduction due to neck pain, followed by LR (34.7%), RR (27.7%), and F (26.7%). The number of velocity peaks (Vpeaks No.) showed the largest group differences in LR with a 44% relative increase in number of velocity peaks. This relative difference in Vpeaks No. of LR was the largest percent of group difference found amongst all outcome measures in all directions. Lesser than for LR but still great increase in Vpeaks No. was found for RR (34.3%), followed by smaller relative group difference for E (24.1%), and for F (22.2%). A mean value of the proportional limitation of symptomatic participants compared to asymptomatic ones (based on significantly group-different measures alone), is presented at the bottom of FIG. 14 for each motion direction. The greatest reduction in velocity and fluency of motion was found during LR-directed motion (38.3%), followed by extension (31.95%) and right rotation (31.6%). Flexion-directed motion demonstrated the least group difference in kinematic measures with only a 26.85% mean group difference.

Reference is now made to FIG. 15 illustrating diagnostic value of significant outcome measures. Results of a logistic regression analysis for kinematic outcome measures, which were found to be statistically significant diagnostic factors, are presented in the figure. The optimal predictor value is provided for each of the listed outcome measures. This is the actual cut off value based on best overall accuracy (i.e., a trade-off between sensitivity and specificity). In Vpeaks No. E, for example, (first row), with every increase of a single peak above 3.5, the chance of being symptomatic is multiplied by a factor of 1.36, e.g. it increases in 36%. Sensitivity and specificity are two key values in diagnostic value analysis, representing the proportion of true positive cases, and true negative cases identified correctly, respectively. Diagnostic values in the figure are sorted by their sensitivity in a descending order. Excellent sensitivity was found for Vpeaks No. in E, with 96% of symptomatic cases (24 out of 25) identified correctly using this predictor. Very good sensitivity was found for Vmax F (88%), and Vmax LR (84%). Good sensitivity was found for Vmean LR (80%), Vmean E (80%), Vmax E (76%), and movement time LR (76%).

The highest specificity was found for movement time F, and for Vpeaks No. LR, with 88% of control cases (37 out of 42) identified correctly. Good specificity was found for Vmean LR (83%), Vmax RR (83%), Vmax E (81%), Vmean RR (81%), movement time RR (81%), and Vpeaks No. F (81%). Lastly, Vmean LR was found most accurate predictor, with 63% accuracy in identifying correctly both control and symptomatic subjects.

An innovative VR assessment method was used to study kinematics of the cervical spine in individuals suffering from neck pain, compared to control subjects. Investigation of cervical kinematics included plotting velocity profiles, evaluating groups' differences, and performing diagnostic value analysis, for each outcome measure.

Results demonstrated a significant reduction in mean and peak velocity of neck motion, longer movement time, and less fluent motion, as performed by the symptomatic participants. Results of logistic regression analysis, using a single predictor, presented the ability of the virtual cervical assessment to distinguish between symptomatic and asymptomatic individuals with high sensitivity and specificity values found for a selected collection of significant predictor measures.

The overall rationale in the development of the VR assessment was to capture and analyze neck motion in a scenario most representative of true neck function. As reported previously, this VR method of assessment provides a reliable and valid tool for ROM assessment, with a significant ROM enhancement effect. The improvement in cervical kinematics displayed with this embodiment of the system indicates that such systems may be used for therapeutic purposes as well. Due to existing recognition that neck pain involves sensory-motor control impairment in addition to ROM limitation, the VR environment seemed ideal for investigation of other kinematical measures of neck motion other than range of motion, such as velocity, motion fluency, response time and time to peak velocity.

One main asset of VR is the interaction between the participant and surrounding images and sounds in the video game displayed inside the HMD. Participation in a VR game can be engaging, motivating, and distracting, all making it hard to focus on other than the interaction task itself. In spite of VR technology applications for medical purposes being a relatively new field, evidence exists to support these advantageous features: VR was found effective in pain distraction and control, including supportive evidence from functional magnetic resonance imaging. VR was demonstrated as a motivating, engaging exercise tool for various purposes, a finding in agreement with recent report of the cervical VR system's ability to enhance cervical motion.

Additional advantages of the presented VR system include programmed components that aim to make the assessment harder to deceive compared to existing assessments based on voluntary motion elicited by oral instruction. The randomized direction of target appearance makes it impossible to predict where target will appear, the pace of targets' disappearance facilitates the participant to act quickly, as the target disappears after 5 seconds.

In contradistinction to the findings of previous studies, significant differences were found between the group of subjects suffering from neck pain and the control group. In particular, subjects suffering from neck pain moved slower and less fluently to virtual targets, than did healthy subjects. Previous studies found no statistical difference between the groups for cervical ROM or peak velocity. Furthermore, previous studies (Sjolander et al.) report lower peak velocity values for rotations (120-1300/s controls vs. 93-1080/s symptomatics) than peak velocity values found using the above described device (162-1660/s controls vs. 100-1090/s symptomatics). The use of the motion assessment system disclosed herein allows for a greater degree of motivation for the subjects to perform than the prior art system such as used by Sjolander et al. in which voluntary motion is elicited by oral instruction. Other systems illustrated in previous studies are similarly limited.

Based on current results the relative limitation in significantly differentiating kinematic measures was calculated. Relative ROM limitation was analyzed previously in the same population and was found to range from 12% to 12.7%2. Greater relative limitation was found in present analysis with 22% to 44% limitation in velocity and fluency of motion parameters. Therefore it seems that in the examined mildly disabled chronic population, motion control represented by velocity and fluency measures was restricted more than the magnitude of motion.

Impaired velocity and fluency of cervical motion in individuals suffering from chronic neck pain is an important finding with clinical implications to diagnostics and management of neck pain. One of the most familiar tools for assessment of disability is the Neck disability index. A modification of the standard questionnaire may be useful including a new item addressing fast cervical motions. In the clinical field, it is suggested that in subjective and physical examination, fast motion of the neck should be examined in addition to spontaneous or voluntary motion. Management strategies may be developed which address the issue of motion control, including training regime that challenge fast, task oriented movements. The presented system may serve as a platform for further development of a VR training system.

Diagnostic value of VR kinematical measures presented the systems ability to identify true positive and true negative cases in the given population, based on kinematical analysis alone. All assessed participants volunteered to the experiment, and had no known secondary gain from participation. Therefore, inclusion and exclusion criteria served as the standard reference for logistic regression analysis.

Measures of No Vpeaks E, Vpeak F, Vpeak LR, Vmean LR, Vmean E (listed in descending order of sensitivity) were found most sensitive with 80%-96% sensitivity and are therefore recommended for identifying true symptomatic individuals suffering from neck pain. VR measures of No Vpeaks LR, movement time F, Vmean LR, Vpeak RR, Vpeak E, Vpeak F, movement time RR, Vmean RR, Vmean E (listed in descending order of specificity) were found most specific with 80%-88% specificity, and therefore may be useful are recommended in identifying true asymptomatic cases, who may not need treatment or may be maligners.

The scope of the present invention is defined by the appended claims and includes both combinations and sub combinations of the various features described hereinabove as well as variations and modifications thereof, which would occur to persons skilled in the art upon reading the foregoing description.

In the claims, the word "comprise", and variations thereof such as "comprises", "comprising" and the like indicate that the components listed are included, but not generally to the exclusion of other components.

The invention claimed is:

1. A method for assessing a kinematic parameter of cervical motion in a subject, the method comprising the steps of:
   (a) stimulating repeated and continuous cervical movements in said subject, with no return to a stationary mid-position, and until said subject fails to increase a cervical range of motion (CROM), wherein the stimulating is performed by displaying to said subject an interactive video game on a surround display, said interactive video game providing events to which said subject reacts;
   (b) three dimensional monitoring of said cervical movements by a three dimensional tracking device, said tracking device comprises a sensor placed about said subject; and
   (c) analyzing data received from said tracking device by a processor.

2. The method of claim 1, wherein said repeated and continuous cervical movements are faster than spontaneous or voluntary movements of said subject.

3. The method of claim 1, wherein said cervical movements comprise cervical extension, cervical flexion, cervical rotation, cervical lateral flexion, or any combination thereof.

4. The method of claim 1, wherein said kinematic parameter comprises movement time, response time, peak velocity, mean velocity, time of peak, jerk, accuracy, smoothness, range of motion, or any combination thereof.

5. The method of claim 1, wherein said three dimensional monitoring comprises monitoring a linear movement, a rotational movement, an angular movement, or any combination thereof.

6. The method of claim 1, wherein said subject is afflicted with cervical motion impairment.

7. The method of claim 6, wherein said cervical motion impairment is neck pain, limited cervical motion, or a combination thereof.

8. The method of claim 1, wherein said surround display is placed in a manner that blocks peripheral distractions.

9. The method of claim 1, wherein said tracking device is an electromagnetic tracking device.

10. The method of claim 1, wherein said stimulating further comprises utilizing a scaling factor for manipulating the appearance of objects in said interactive video game.

* * * * *